US005593719A

United States Patent [19]
Dearnaley et al.

[11] Patent Number: 5,593,719
[45] Date of Patent: Jan. 14, 1997

[54] TREATMENTS TO REDUCE FRICTIONAL WEAR BETWEEN COMPONENTS MADE OF ULTRA-HIGH MOLECULAR WEIGHT POLYETHYLENE AND METAL ALLOYS

[75] Inventors: Geoffrey Dearnaley; James Lankford, Jr., both of San Antonio, Tex.

[73] Assignee: Southwest Research Institute, San Antonio, Tex.

[21] Appl. No.: 220,234

[22] Filed: Mar. 29, 1994

[51] Int. Cl.$^6$ .............................. B05D 3/00; A61F 2/30; C23C 14/12; B29C 37/00
[52] U.S. Cl. .................. 427/2.26; 427/525; 427/527; 427/530; 427/528; 427/296; 427/307; 216/83; 623/18; 623/19; 623/20; 623/22
[58] Field of Search ............................. 427/2, 527, 525, 427/530, 528, 296, 307, 308, 316, 222, 2.24, 2.26, 534; 156/668; 623/18, 19, 20, 21, 22, 23; 216/83, 7

[56] References Cited

U.S. PATENT DOCUMENTS

| | | | |
|---|---|---|---|
| 3,622,440 | 11/1971 | Snedeker et al. | 161/193 |
| 3,717,522 | 2/1973 | Shirato et al. | 156/53 |
| 4,362,681 | 12/1982 | Spector et al. | 427/2.26 |
| 4,410,611 | 10/1983 | MacIver | 427/525 |
| 4,452,827 | 6/1984 | Kolev et al. . | |
| 4,465,715 | 8/1984 | Manabe et al. | 427/307 |
| 4,486,286 | 12/1984 | Lewin et al. . | |
| 4,495,044 | 1/1985 | Banks . | |
| 4,554,208 | 11/1985 | MacIver et al. | 427/525 |
| 4,647,494 | 3/1987 | Meyerson et al. . | |
| 4,698,236 | 10/1987 | Kellogg et al. | 427/527 |
| 4,725,345 | 2/1988 | Sakamoto et al. . | |
| 4,743,493 | 5/1988 | Sioshansi et al. . | |
| 4,746,538 | 5/1988 | Mackowski . | |
| 4,756,964 | 7/1988 | Kincaid et al. . | |
| 4,770,902 | 9/1988 | Barlow et al. | 427/117 |

(List continued on next page.)

FOREIGN PATENT DOCUMENTS

| | | |
|---|---|---|
| 0548799A1 | 6/1993 | European Pat. Off. . |
| 548788 | 6/1993 | European Pat. Off. ............... 427/525 |
| 62-196371 | 8/1987 | Japan . |
| 62-202897 | 9/1987 | Japan . |
| 1147067A | 6/1989 | Japan . |

OTHER PUBLICATIONS

Brown, Malcolm W., "Diamond Coating May be Future of Tool Manufacture," Article in San Antonio Express News (April 1, 1996).

R. S. Butter et al., "Diamond–Like Carbon for Biomedical Applications," Applied Diamond Conference (Aug. 21–24, 1995), pp. 683, 688 and 690.

J. Lankford, et al., *Adherence of Diamondlike Carbon Coatings on Total Joint Substrate Materials*, Nuclear Instruments and Method in Physics Research B80/81, Part II, 1441–1445 (1993) No Month.

(List continued on next page.)

*Primary Examiner*—Marianne Padgett
*Attorney, Agent, or Firm*—Niadan & Morris

[57] ABSTRACT

The present invention provides methods for modifying surfaces made from metal alloy and/or UHMWPE, preferably surfaces which are frictionally engaged, e.g., in an orthopaedic implant. The methods of the present invention reduce the coefficient of friction of the metal alloy component, reduce the shearing of fibrils from the UHMWPE component, and reduce sub-surface fatigue in the UHMWPE component. The method involves solvent immersion of the UHMWPE component to remove short chains of polyethylene at or near the surface of the component, and to swell and toughen the subsurface of the component. The method also involves firmly coating the surface of the metal alloy component with an adherent layer of diamond-like carbon ("DLC") by creating a metal-silicide interface at the surface of the metal alloy to permit firmer adhesion of DLC. Although the methods of the present invention are particularly useful in orthopaedic applications, the methods also can be used to treat similar components used in other applications.

38 Claims, 2 Drawing Sheets

U.S. PATENT DOCUMENTS

| | | |
|---|---|---|
| 4,772,513 | 9/1988 | Sakamoto et al. . |
| 4,778,469 | 10/1988 | Lin et al. . |
| 4,822,355 | 4/1989 | Bhuvaneshwar ............................ 623/2 |
| 4,822,466 | 4/1989 | Rabalais et al. . |
| 4,842,937 | 6/1989 | Meyer et al. . |
| 4,877,677 | 10/1989 | Hirochi et al. . |
| 4,961,958 | 10/1990 | Desphandey et al. . |
| 4,966,803 | 10/1990 | Pluyter et al. .......................... 428/192 |
| 4,981,071 | 1/1991 | Enke ........................................ 427/573 |
| 5,009,923 | 4/1991 | Ogata et al. . |
| 5,028,451 | 7/1991 | Ito et al. . |
| 5,064,682 | 11/1991 | Kiyama et al. . |
| 5,084,151 | 1/1992 | Vallana et al. . |
| 5,130,161 | 7/1992 | Mansur et al. . |
| 5,133,757 | 7/1992 | Sioshansi et al. . |
| 5,133,845 | 7/1992 | Vallana et al. . |
| 5,135,808 | 8/1992 | Kimock et al. . |
| 5,169,597 | 12/1992 | Davidson et al. ......................... 623/16 |
| 5,176,710 | 1/1993 | Hahn et al. . |
| 5,192,330 | 3/1993 | Chang et al. . |
| 5,192,523 | 3/1993 | Wu et al. . |
| 5,219,363 | 6/1993 | Crowninshield et al. . |
| 5,228,451 | 7/1993 | Bales et al. . |
| 5,252,174 | 10/1993 | Deguchi et al. ......................... 427/527 |
| 5,270,252 | 12/1993 | Papanicolaou .......................... 437/176 |
| 5,314,492 | 5/1994 | Hamilton et al. . |
| 5,391,407 | 2/1995 | Dearnaley ................................ 427/528 |
| 5,393,572 | 2/1995 | Dearnaley ................................ 427/523 |
| 5,415,704 | 5/1995 | Davidson ................................ 623/16 |
| 5,425,777 | 6/1995 | Sarkisian et al. . |
| 5,480,683 | 1/1996 | Chabrol et al. ......................... 427/2.26 |
| 5,515,590 | 5/1996 | Pienkowski ............................ 427/2.26 |

OTHER PUBLICATIONS

John H. Dumbleton, Ph.D., *The Clinical Significance of wear in Total Hip and Knee Prostheses*, Journal of Biomaterials Applications, vol. 3, Jul., 1988, 3, 10–32.

G. Dearnaley, et al., *Bioapplications of Diamond–like Carbon Coatings*, "4th World Biomaterials Congress", Berlin, Apr., 1992.

A. M. Jones, et al., *Stress and Microstructure of Diamond–like Carbon from Ion–beam Decomposition of Hydrocarbon Precursors*, 2nd European Conference on Diamond, Diamond–like and Related Coatings, Nice, France, Sep. 2–6, 1991.

C. J. Bedell, et al., *Diamond–like Carbon from the Ion–beam Decomposition of Polyphenyl Ether*, Applications of Diamond Films & Related Materials, 833–838 (1991) No Month.

J. A. Davidson, Ph.D., et al., *Surface Modification Issues for Orthopaedic Implant Bearing Surfaces*, Surface Modification Technologies V, 1–14 (1992) No Month.

P. Bodo, et al., *Adhesion of Evaporated Titanium to Polyethylene: Effects of ion Bombardment Pretreatment*, J. Vac, Sci. Technol. A 2 (4), Oct. Dec. 1994, 1498–1502.

*Polymer*, 1992 (No Month), vol. 33, #19 pp. 4075–4080 P. Gao, et al., "Surface Treatment of Ultra High Molecular Weight Polyethylene to Enhance Adhesion and Conductivity Properties".

A. C. Evans, et al., "Diamond–like Carbon Applied to Bioengineering Materials", *Medical Device Technology*, May 1991, 26–29.

C. M. Agralwal, et al., *The Effects of Diamond–like–carbon Coatings on the Friction and Wear of Enhanced UHMW–PE–metal Couples*, 19th Annual Meeting of the Society for Biomaterials, Apr. 28–May 2, 1993.

Wieluński et al "Improvements of Thermally formed Ni$_2$Si by ion irradiation", *J. Vac. Sci. Technol.* 20(2) Feb. 1982 pp. 182–185.

TREATMENTS TO REDUCE FRICTIONAL WEAR BETWEEN COMPONENTS MADE OF ULTRA-HIGH MOLECULAR WEIGHT POLYETHYLENE AND METAL ALLOYS

FIELD OF THE INVENTION

The present invention relates to decreasing frictional wear and degradation in products, typically orthopaedic implants, in which components made from ultra-high molecular weight polyethylene (UHMWPE) come into frictional contact with components, e.g., made of a metal alloy, such as cobalt-chromium.

BACKGROUND OF THE INVENTION

The replacement of destroyed or damaged human joints is one of the great achievements of twentieth century orthopaedic surgery. However, total joint prostheses, composed of various combinations of metal, ceramic, and polymeric components, continue to suffer from distressingly limited service lives. For example, the current generation of high-load bearing prostheses for the hip and knee have a typical lifetime on the order of 6–12 years. Generally, failed implants can be replaced once or twice, which means that current technology provides a solution for—at most—about 25 years.

With human life expectancies steadily increasing, there is a driving need to increase significantly the effective lifetime of a single implant. One of the problems encountered in designing such prostheses is the difficulty of finding materials which are both biocompatible and also durable enough to replace a human joint. In use, a human joint is exposed to substantial, repetitive loads and frictional stresses.

Although the geometric details may vary, a natural human hip, knee, or shoulder joint generally includes: (a) a more-or-less spherical ball; (b) an attachment to a long bone; and, (c) a hemispherical socket (the "acetabular cup") in a contiguous bony structure which retains the spherical ball so that the long bone may pivot and articulate. In a healthy joint, nature minimizes the friction between the joint components and prevents bone-on-bone wear and destruction by using mating porous cartilaginous layers that provide "squeeze-film" synovial fluid lubrication. This lubrication results in a low coefficient of friction on the order of 0.02.

When a human joint has been destroyed or damaged by disease or injury, surgical replacement (arthroplasty) normally is required. A total joint replacement includes components that simulate a natural human joint, typically: (a) a more-or-less spherical ceramic or metal ball, often made of cobalt-chromium alloy; (b) attached to a "stem," which generally is implanted into the core of the adjacent long bone; and (c) a hemispherical socket which takes the place of the acetabular cup and retains the spherical ball. This hemispherical socket typically is a metal cup affixed into the joint socket by mechanical attachments and "lined" with UHMWPE so that the ball can rotate within the socket, and so that the stem, via the ball, can pivot and articulate.

One of the difficulties in constructing any device for implantation into the human body is the need to avoid an adverse immune response. The possibility of an adverse immune response is reduced when certain synthetic materials are used. Cobalt-chromium alloy, titanium, and UHMWPE are examples of such synthetic materials. Unfortunately, the use of UHMWPE in the bearing of a total joint replacement may be the cause of at least one type of failure of such devices.

Three basic problems may cause a total joint replacement to fail or to have a limited service life. The first problem, which manifests itself at the bone-stem interface, is not the focus of the present application. Because the elastic modulus of the stem greatly exceeds that of the bone, flexural loading caused by walking creates local cyclic stress concentrations due to the non-compliance of the stem. These stresses can be intense and even severe enough to cause death of local bone cells. If this occurs, pockets of non-support are created, and the stem may loosen or fail.

The two other basic problems, which are coupled, are the subject of the present application. One of these problems, known as ball-cup friction and wear, results from frictional wear between the hemispherical bearing (which is "lined" with UHMWPE) and the polished spherical ceramic or metal ball attached to the stem. The other problem, known as sub-surface fatigue, results from brittleness of the UHMWPE bearing and the resulting tendency of the UHMWPE bearing to fail under reciprocating applied loads.

For many years, the acetabular cup in joint implants has been "lined" with UHMWPE, or other materials, in order to decrease the coefficient of friction of the socket or bearing. Unfortunately, clinical experience has shown that, at least when UHMWPE is used to line the bearing, either the surface of the UHMWPE "bearing" and/or the surface of the metal/ceramic ball ultimately is destroyed by friction-induced wear. Alternately, the acetabular cup loosens after a period of use, greatly increasing ball-cup friction and wear.

Some insight into the cause of failure due to ball-cup friction and wear has been gleaned from histological studies of the surrounding tissue. These histological studies show that the surrounding distressed tissue typically contains extremely small particles of UHMWPE which range from sub-micrometers to a few micrometers in size. Larger particles of UHMWPE appear to be tolerated by the body, as is the solid bulk of the UHMWPE bearing. However, the body apparently does not tolerate smaller particles of UHMWPE. In fact, these small particles of UHMWPE cause powerful histiocytic reactions by which the body unsuccessfully attempts to eliminate the foreign material. Agents released in this process attack the neighboring bone to cause "wear debris-induced osteolysis" which, in turn, leads to a loss of fixation and loosening of the prosthesis due to "remodeling" of the bone.

The first step in the generation of the small particles of UHMWPE appears to be the formation of a very thin layer of polyethylene between the spherical ball and the UHMWPE lining of the bearing. This thin film of polyethylene adheres to the "ball" and serves as a soft, shearable, solid lubricant composed of millions of submicrometer particles. Adhesive wear between the ball and the bearing produces strong, adhesive junctions on the ball. When exposed to further friction, fibrils of the polymer shear off of these adhesive junctions and are drawn into slender connecting ligaments, eventually producing ligament rupture.

This ligament rupture apparently produces the lubricous, extremely small particles of UHMWPE which eventually migrate to the bone-acetabular cup bond line. The reason for migration of these particles into the "crevice" between the ball and the cup are the microcurrents that are generated in the synovial fluid by joint motion. Once a sufficient number of small particles enter the bone-cup crevice, the bone tissue begins to degrade and the joint replacement eventually loosens and fails.

One way to reduce friction between the metal and UHMWPE components would be to coat one or both of the components with diamond-like carbon (DLC), which is chemically inert, biocompatible, and is known to have a low coefficient of friction. Unfortunately, the very properties of DLC that make it a desirable coating for parts that will be frictionally engaged make it difficult to achieve strong adhesion of the DLC coating to the substrate, particularly where deposition temperatures must be low. This limited adhesion problem can be exacerbated by very high compressive stress, such as that found in a plasma-deposited DLC (up to 8 GPa). Therefore, some have concluded that DLC—or at least plasma-deposited DLC—cannot be used in orthopaedic applications.

Energetic ion beam-associated DLC has a far lower residual stress than plasma-deposited DLC, and is a better candidate for a high integrity DLC. The substrate material to which all forms of carbon adhere most successfully is silicon. This is because strong covalent Si—C bonds are easily formed between the coating and the silicon substrate. Some have attempted to improve the adhesion of DLC to other materials, such as metal alloys, by forming an interposed silicon bond-coat to which the DLC will adhere more strongly.

Unfortunately, this simple approach does not result in adhesion that survives in applications, such as orthopaedic applications, where the DLC coating is subjected to substantial friction and stress. The simple formation of a silicon bond-coat on a metal alloy appears to create another relatively weak interface between the silicon and the metal or alloy.

Therefore a method is needed by which a DLC coating can be strongly adhered to a metal surface, and by which the shearing of polymer fibrils from an UHMWPE component can be prevented. The method would be most efficient if it rendered the UHMWPE compound less brittle so that sub-surface fatigue failure was reduced.

SUMMARY OF THE INVENTION

The present invention provides a method for modifying the surfaces involved, typically a metal alloy spherical ball and an UHMWPE bearing, to reduce: (1) frictional wear between such surfaces; (2) shearing of fibrils from the UHMWPE bearing; and (3) sub-surface fatigue in the UHMWPE component. The method involves solvent immersion of the UHMWPE component to remove short chains of polyethylene at or near the surface of the component, and to swell and strengthen the subsurface of the component. The method also involves treating the metal alloy spherical ball to create a metal-silicide interface which permits firmer adhesion of DLC and thereby reduces the coefficient of friction of said surface. Although the methods of the present invention are particularly useful in orthopaedic applications, the methods also can be used to treat similar components used in other applications.

DETAILED DESCRIPTION OF THE INVENTION

The present invention has two aspects. The first aspect is solvent immersion treatment of the UHMWPE component. The second aspect is a method for creating strong adhesion of the DLC coating to the spherical ball.

Solvent Immersion of UHMWPE Component

Solvent immersion according to the present invention may be used to treat any UHMWPE component that will be exposed to friction during use in order to increase the life of such a component. Solvent immersion particularly is useful in connection with medical devices, and most particularly with medical devices such as total joint replacements, which contain UHMWPE bearings that will be exposed to friction during use.

Methods of manufacturing components made of UHMWPE are known. The process of the present invention preferably is performed after the component has been formed, but before insertion into an end product, such as the metal cup of a total joint prosthesis. The apparatus used to immerse the UHMWPE component is not critical to the present invention. For example, if desired, the UHMWPE component may be immersed in the solvent using a simple hand-held instrument.

A preferred solvent for immersion according to the present invention is decahydronaphthalene ($C_{10}H_{18}$, anhydrous), also known as Decalin™. However, other organic solvents which are capable of dissolving short chain polyethylenes and of swelling the microstructure of the component also may be used. Such solvents include aromatic hydrocarbons, such as benzene, toluene, xylene, and o-dichlorobenzene; other alicyclic hydrocarbons, such as cyclohexane and tetrahydronaphthalene, also known as Tetralin™; and, aliphatic hydrocarbons such as n-paraffin, isoparaffin, and mixtures thereof.

The solvent chosen should be placed in an appropriate container for immersion of the UHMWPE component under controlled conditions of time and temperature. The solvent should be heated to a temperature that will maximize the dissolution of short polyethylene chains, typically between about 30°–100° C. A temperature of between about 30°–50° C. is preferred because temperatures above about 50° C. result in excessive swelling of the polymer. Once a stable solvent temperature has been reached, the UHMWPE component should be immersed and retained in the solvent for a period sufficient to dissolve any short chain polyethylenes and to swell the microstructure of the component. This typically should require about 30–180 seconds, preferably about 30 seconds. The time of immersion generally should decrease as the temperature of the solvent is increased.

After the UHMWPE component has been immersed in the solvent for an appropriate period of time, the component should be removed from the solvent and allowed to dry. A "naked" UHMWPE component generally should be dried for about 24 hours at room temperature. The conditions under which the UHMWPE component is dried are not critical; however, if the UHMWPE component has areas that are difficult to dry, some relatively mild form of heat or air flow may be helpful to dry the component.

After the UHMWPE component has been dried, the UHMWPE component should be placed in a standard vacuum chamber and exposed to a vacuum of between about $10^{-1}$–$10^{-5}$ torr, preferably about $10^{-3}$ torr, for a time sufficient to remove residual solvent, preferably at least 8 hours. Thereafter, the UHMWPE component is ready for assembly into an end product and/or for any further treatment(s) that may be required before use, e.g., sterilization.

DLC COATING OF METAL COMPONENT

The method for treating a metal alloy to provide a diamond-like coating (DLC) uses ion beam assisted deposition of silicon, followed by deposition of DLC. This method is believed to form strong interatomic bonds across the DLC coating-substrate interface. In order to knit the successive layers of metal-silicon-DLC together effectively, it is necessary to supply a bond-interface for the metal-silicon bond as well as for the silicon-DLC bond. Without limiting the present invention, it is believed that the present method achieves this result by forming strong interatomic bonds having a character that is intermediate between the type of bond that exists between the atoms in the metal and the type of bonds in the silicon. Preferably, a metal substrate is used that forms a strongly-cohesive silicide—that is, an intermetallic compound in which the bonding is partially metallic and partially covalent. Metal substrates that form strongly-cohesive silicides include cobalt, nickel, titanium, zirconium, chromium, molybdenum, tungsten, platinum, and palladium.

After conventional cleaning of the component to remove superficial contaminants, such as grease, the component is placed in a vacuum chamber that has been evacuated to a base pressure of preferably less than $10^{-5}$ torr. The component then is bombarded with ions, preferably argon ions, at an energy range between about 10–100 keV, preferably around 10 keV. This ion bombardment provides an effective means to remove some of the remaining adsorbed atoms from the surface.

The component is heated, preferably to a temperature of about 300° C., or, if the material is temperature sensitive, to the highest temperature acceptable for that material. Silicon then is deposited onto the component using known means. A preferable means is to position the workpiece directly over the volatilization hearth which is maintained at a preferred temperature of about 750° C. (1382° F.), until a preferred coating thickness of between 100–200 nm has been achieved. The thickness of the coating may be monitored by standard methods, e.g., using the frequency charge of a quartz crystal oscillator.

The component preferably is simultaneously bombarded with an energetic beam of ions, preferably argon ions, at an energy range between 500 eV to 100 keV, preferably between 10–20 keV, in order to form a layer of metal silicide at the metal-silicon interface. Although argon ions are preferred, other suitable ions may be used, such as nitrogen, argon, hydrogen, silicon, methane, helium, or neon, having an energy between 500 eV to 100 keV, preferably 10–30 keV. The ion-to-atom ratio should be sufficient, preferably at least 1 ion to 10 silicon atoms, to form a layer of metal silicide at the metal-silicon interface.

Thereafter, the component is cooled to about 80° C., preferably without removing the component from the vacuum chamber, and the diamond-like carbon (DLC) is deposited, preferably using energetic ion beam deposition techniques. The DLC preferably should be deposited by vaporizing a precursor, such as polyphenyl ether, and condensing the precursor onto the surface of the component using known means. At the same time, the component should be bombarded, either in a continuous or interrupted fashion, with an energetic beam of ions. Preferable ions are nitrogen, argon, hydrogen, silicon, methane, helium, or neon, having an energy between 500 eV to 100 keV, preferably 10–30 keV. The procedure is continued until a thickness of DLC between about 100 nm–10 microns is achieved.

EXAMPLES

GENERAL EXPERIMENTAL PROCEDURES

Wear Test Machine

Figure 1:
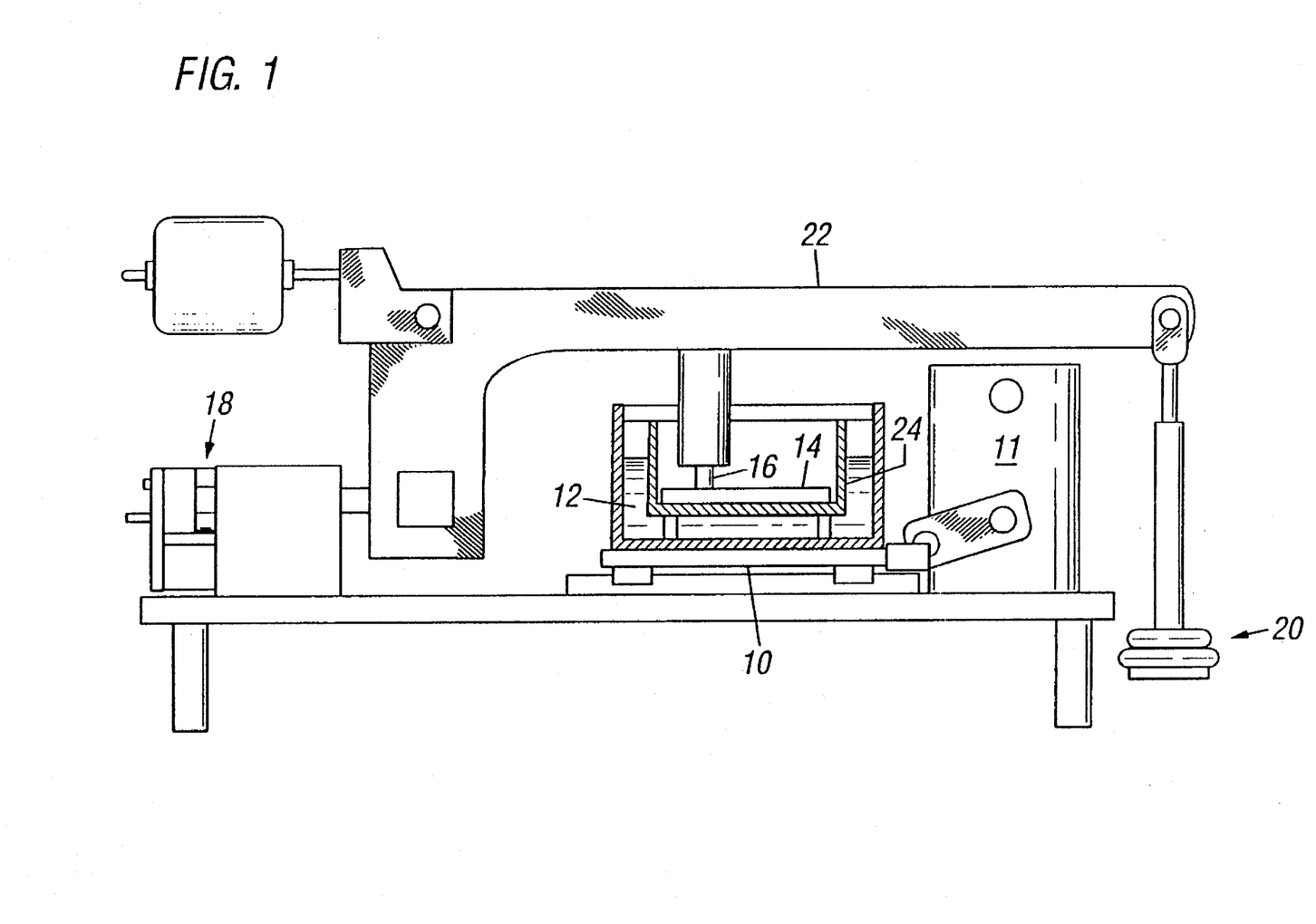
FIG. 1 is a diagrammatic representation of a mixed prospective and cross sectional side view of the wear test machine used in the following experiments.

The wear test machine used in the following examples provided a versatile means for material wear testing. The machine, which is shown in FIG. 1, was capable of applying user defined load profiles in a temperature controlled environment. Briefly, the wear test machine included a reciprocating table 10 controlled by a drive 11. On the reciprocating table 10 was a water bath 12 which held the plate 14 to be tested. A pin 16, described more fully below, was retained stationary adjacent to or abutting the plate 14 or sample to be tested. The movement and weight exerted on the plate 14 by the pin 16 was controlled by a force transducer 18 and a dead weight 20, as described more fully below.

Reciprocating Motion

Linear reciprocating motion was accomplished by means of the DC servo motor drive 11 (configured in velocity mode) directly coupled to a ball screw driven rail table 10. Stroke length was determined by two magnetic control switches mounted on the front of the machine. A trapezoidal velocity profile was sent to the motor as a voltage from a Mackintosh IIci equipped with a data acquisition board and software using a LabVIEW software development system (National Instruments, Austin, Tex.). This trapezoidal velocity profile was under closed loop control using the magnetic control switches as position feedback. The speed of reciprocation was controlled by the magnitude of the trapezoidal voltage signal sent from the Mac IIci.

Load Profiles

Static loads were applied using dead weights 20 placed on the end of a stainless steel beam 22. The normal force on the pin 16 was calculated to be 1.9 times the weight of the dead weights 20 on the end of the beam 22. The maximum static normal force was 43.7 pounds (194.4 N) on the pin [23 pounds (102.3 N) located at the end of the beam 22].

Force Measurements

Frictional force recordings between the pin and the plate were obtained from a piezoelectric, voltage mode force transducer. Since the capacity of the force transducer was 100 lbs (444.8 N), very small force measurements could be inaccurate. Normal force recordings on the pin 16 were obtained from a piezoelectric, voltage mode force transducer 18. Its capacity also was 100 lbs (444.8 N).

Cycle Count

The number of cycles was counted in two places. On the Mac IIci, a software counter was incremented each time the left magnetic control switch was closed. As a hardware backup mechanism, a separate magnetic switch (which used the same power supply as the control switches) was located on the back of the wear machine to increment an electronic counter.

Temperature

The temperature of the wear environment could be regulated by means of a water bath 12 which surrounded the stainless steel wear chamber 24. The water bath 12 was heated by a stainless steel immersion heater controlled by a temperature controller. Water temperature was measured with an RTD probe placed in the bath.

Safety

Since it was desirable for the wear machine to operate overnight and on weekends without supervision, a number of safety mechanisms were used.

Software Control

The computer program which drove the system had a "stop switch" on the screen which enabled the program to be manually stopped at any time. Also, the program continually sampled from two additional magnetic stop switches inside the reciprocating rail table. Therefore, in the event of the stroke length being exceeded, one of these switches would close and the program would be stopped. These two stop switches were located slightly outside of the desired stroke length of the wear test (which was determined by the two magnetic control switches previously discussed).

Hardware Control

Located outside of these stop switches were two industrial mechanical push button switches placed in series between the main power source and the motor drives. These switches normally were closed.

If the reciprocating table 10 traveled too far beyond the desired stroke length of the wear test, one of the magnetic stop switches closed, which caused the computer program to send zero volts to both DC motors 11, stopping the wear test. However, a very small voltage still was sent to the motors 11 from the computer, to which the velocity-configured motor 11 could respond. Therefore, the wear chamber 24 continued slowly to drift and soon engaged one mechanical stop switch. This engagement turned off the main power to the motors 11.

Evaluation of Wear

Evaluation of wear resistance and the associated coefficient of sliding friction was performed under realistic environmental but static loading conditions. Two types of wear were measured. First, the wear represented by loss of the coating from the substrate, which was quantified in terms of the number of cycles required to expose the substrate, or major portions thereof. This determination was most effectively made by microscopic observation, rather than by weight loss.

In cases where no coating was involved, it was useful to monitor weight loss; however, it was imperative to compensate for environmental fluid uptake (gain in mass) of the wear sample by using a dummy sample presoaked and exposed to the test bath simultaneously alongside the wear specimen. To ensure that trends observed in the data represented a steady state situation, data was obtained over a period approaching $10^6$ cycles (corresponding to about one year of normal ambulation). Later tests completed about $1.25 \times 10^6$ cycles.

Simulation of Joint Environment

The environment of a natural joint (with synovial fluid) was simulated using bovine serum. Pin/plate materials were chosen based on a judgment that the constraints of the total joint design cause a localized sector of the femoral ball to describe a wide path within the socket of the acetabular component. Eventually, as seen in joint simulator experiments, a millimeter or more of polymer may be worn away, with no measurable loss of material by the metal or ceramic ball. Therefore, these tests utilized metal, ceramic, or coated metal pins run against coated or uncoated polymeric plates.

Polyethylene

The virgin UHMWPE that was used in the following examples was obtained from Westlakes Plastics, Lenni, Pa. For purposes of the present study, gamma-ray sterilization was not performed. If such sterilization had been performed, then the sterilization process should have produced a marginal improvement of mechanical performance, as a consequence of cross-linking. Because the surface of polyethylene is scratched easily, all of the surfaces and materials were kept scrupulously clean using a laminar air-flow cabinet. A Struers Rotopol polisher with a Pedamat head was used to polish the samples according to the procedure given in Table I:

TABLE I

Polishing of Polyethylene

| Step | Abrasive | Applied Load | Duration |
|---|---|---|---|
| 1. | 400 grit SiC | 100 N | 2 min. repeat once |
| 2. | 600 grit SiC | 100 N | 2 min. repeat once |
| 3. | 1200 grit SiC | 100 N | 2 min. repeat once |
| 4. | 2400 grit SiC | 100 N | 2 min. repeat once |
| 5. | 4000 grit SiC | 100 N | 2 min. repeat once |
| 6. | 1 µm Diamond Spray on Pan-w Cloth* | 80 N | 5 min. repeat until scratches are gone |

*Pan-w is a cardboard like cloth made by STRUERS.

The alloy was manufactured by Carpenter Technology, Houston, Tex., and had the following composition: cobalt 70/chromium 30, with a minor addition of molybdenum. After machining, the 10 mm diameter test pins were contoured at one end to a radius of 20 mm and polished by standard metallurgical techniques. The curvature was designed to prevent the edge of the pin from cutting into the surface of the polyethylene flat.

Wear testing was performed using the wear test machine described above. The temperature was maintained within the test chamber at 23±1° C. by means of an external water bath 12. The chamber containing the sample plate 14 was reciprocated beneath the stationary pin 16 at 1 Hz over a sliding distance of 50.8 mm per cycle; both sliding speed and distance approximate that which obtains during service within a total hip joint. Cobalt-chromiummolybdenum and alumina pins 16 were machined to a 20 mm radius (similar to that of typical femoral balls) and polished metallographically to obtain a surface finish of less than 0.05 um $R_a$.

Samples were soaked in pairs (wear specimen plus dummy) for one week in bovine serum buffered with sodium azide in a 0.1 vol. % solution, the latter to prevent bacterial growth. Subsequent wear testing was performed in the same solution, and the soaked control specimen was used to correct for fluid weight gain in the wear sample. Samples were weighed periodically during testing, and corresponding associated friction coefficients (ratio of linear force to normal load) were measured during sliding.

The desired test load, and that used for most experiments, corresponded to a stress level induced by normal body loads at a total hip interface. Since the articulating pin-on-plate wear surfaces did not conform to the degree of the actual prosthesis, the required equivalent stress loads were lower. In particular, using the measured plastic impression within a UHMWPE plate as a measure of contact area, the approximate equivalent (stress) load was 33.4 N.

Tests generally were run for $10^6$ cycles, with wear defined in terms of cumulative mass (volume) loss. Samples were examined by scanning electron microscopy (SEM) at the conclusion of the test.

Solvent Immersion

The polished samples were treated with Decalin™ for between 30 seconds at 120° C. and 3 minutes at 50° C., as shown in Table II. The higher temperatures resulted in excessive swelling of the polymer. From the following results, it was concluded that it might be possible to use Decalin™ at room temperature to achieve adequate selective dissolution of the low molecular weight polyethylene fraction.

Figure 2:
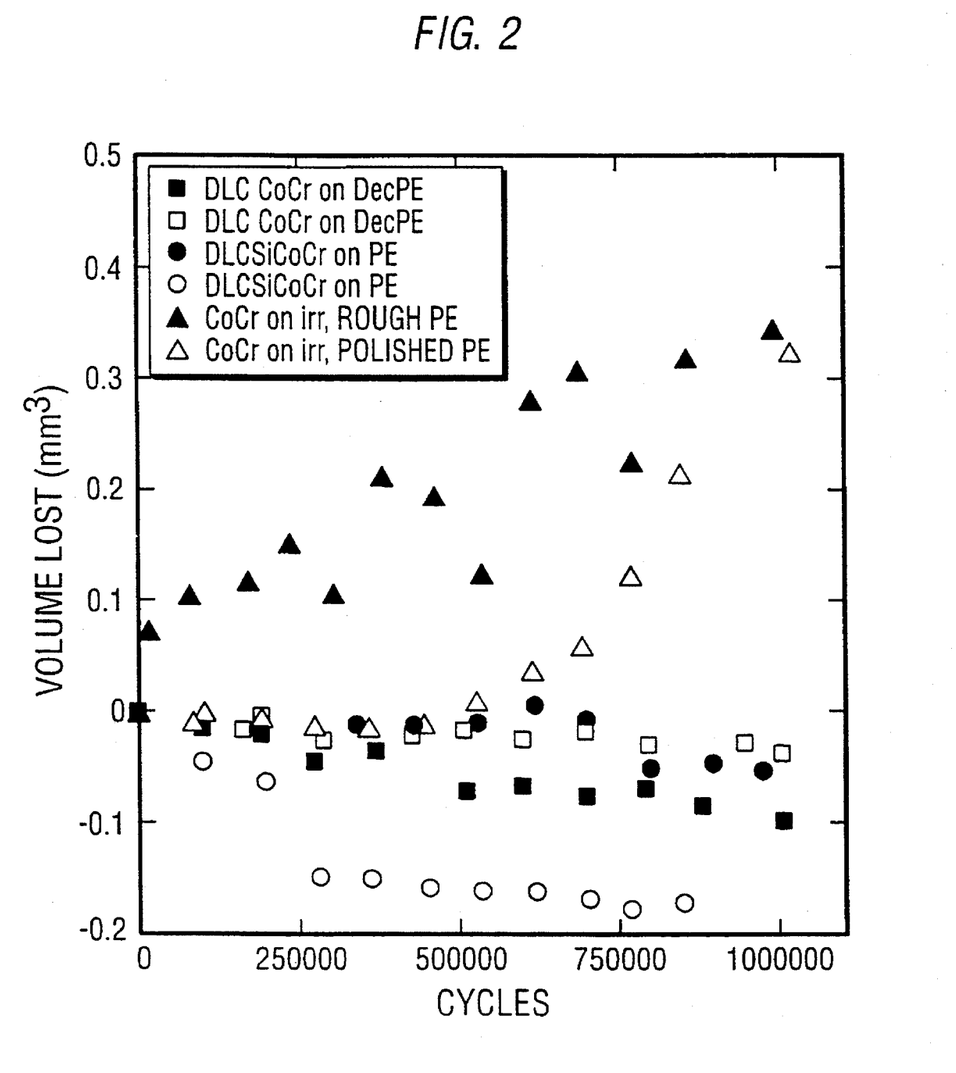
FIG. 2 is a chart of the number of wear cycles against the volume ($mm^3$) lost during those cycles.

For CoCr—DLC against Decalin™-treated polyethylene, as well as for CoCr—DLC against untreated polyethylene, wear virtually was zero for more than one million cycles; however, major wear was observed for CoCr against untreated UHMWPE. In addition, it was observed that wear of CoCr on highly polished UHMWPE only occurred following an incubation period of approximately 500,000 cycles, versus the immediate wear measured for CoCr against rough polished (commercial quality finish) polyethylene. Unfortunately, once wear begins, the wear can be so rapid that the cumulative wear volumes for rough and smooth surfaces are essentially equal by approximately 1.5 million cycles. Therefore, the advantage achieved by polishing alone is short-lived, and ultimately inconsequential, due to the devastating wear rate associated with fibrillar pullout/failure. In both cases, wear surfaces exhibited fibrillar pullout and microfailure. These observations are quantified in FIG. 2, which shows actual wear rate and wear factors (wear volume normalized for load) for all cases. These wear rates and wear factors for the CoCr-UHMWPE cases are in close agreement with data generated under similar conditions and reported in H. A. McKellop, et al., "Wear Characteristics of UHMWPE," J. Biomed. Mater. Res., 12 (1978) 895.

For the minimal wear cases, a groove caused by creep deformation was produced in the plates, but no weight loss was measured. At $10^6$ cycles, sliding contact surfaces of the Decalin™-treated UHMWPE had become gently undulating, with fine-scale, very flat deformation (but not wear) markings superimposed on the undulations. The original surface was flat (no undulations) and covered with fine-scale polish markings. The latter contrasts with the original polished surface of untreated polyethylene, which was characterized by fibrillar structures similar to those observed during equilibrium wear.

Although likewise characterized by zero measured wear for at least $1.25\times10^6$ cycles, the contact microtopography for smooth-polished DLC against CoCr—DLC had a markedly different appearance. Undulations were not so apparent, and material appeared to have been pulled out of the surface. However, high magnification study of these structures indicated that they were fairly flat, unlike the sharply-peaked, tensile-failure, fibrillar structures observed for uncoated CoCr against UHMWPE. This suggested that the forum landmarks probably did not yet correspond to wear (detachment from the substrate).

The results of the test, given in Table II, show that after $10^6$ cycles, no fibrils were present at the wear surface of Decalin™ treated polyethylene:

DLC Coating

Example 1

A DLC coating of approximately 1 micron in thickness was prepared by nitrogen ion bombardment of a polyphenyl ether precursor. The alloy was cleaned in isopropyl alcohol prior to coating. Isopropyl alcohol was chosen because it leaves few, if any, residues. Wear testing revealed that, under some circumstances, there could be a loss of adhesion of the coating.

Example 2

A later batch of four CoCr pins was treated using a bond-coat of silicon. Silicon was chosen because (a) DLC is known to adhere better to silicon that any other substrate, which is attributed to strong SiC bonds formed at the interface, and (b) cobalt and, to a lesser extent, chromium are known to form silicides ($CoSi$, $CoSi_2$, $CrSi_2$) at the interface if the temperature exceeds about 300° C. This solid state reaction is known to be enhanced by ion assisted deposition, probably because energetic ions disrupt the surface oxide or other barriers to interdiffusion at the metal-silicon interface.

Therefore, a coating process was chosen which was an argon ion-assisted deposition of approximately 100 nm of silicon at 300° C. The silicon was evaporated from an electron-beam heated hearth and the thickness was controlled by means of a quartz crystal film thickness monitor (Intellimetrics Ltd.). DLC was deposited, in a separate run. After initial ion bombardment in the vacuum chamber to remove the remaining adsorbed atoms from the surface, the alloy was heated to a temperature of 300° C. The DLC thickness achieved was approximately 0.5 microns.

In prolonged wear tests, at a contact pressure of 6.9 MPa against UHMWPE under serum, i.e., load and environmental conditions equivalent to walking, no decohesion or loss of DLC was observed after 1.25 million reciprocated wear cycles.

Conclusions

DLC coated CoCr against polyethylene clearly represents a considerable advantage over uncoated CoCr against polyethylene. Moreover, pretreatment of the UHMWPE with

TABLE II

| Pin | Plate | Load (N) | μ | N (cycles) | Wear |
|---|---|---|---|---|---|
| CoCr-DLC | UHMWPE Decalin ™ Pretreat 30 s at 100° C. | 33.4 | 0.12 | 537,498 | ~0 |
| CoCr-DLC | UHMWPE Decalin ™ Pretreat 30 s at 100° C. | 33.4 | 0.135 | 1,000,610 | ~0 |
| CoCr-DLC | UHMWPE Decalin ™ Pretreat 180 s at 50° C. | 33.4 | 0.11 | 1,000,000 | ~0 |
| CoCr-DLC | UHMWPE | 33.4 | 0.08 | 1,000,000 | ~0 |
| CoCr | UHMWPE (rough polish) | 33.4 | 0.09 | 1,000,000 | major |
| CoCr | UHMWPE (smooth polish) | 33.4 | 0.14 | 1,000,000 | major, following incubation period of ~5 × 10⁵ cycles |
| CoCr-DLC | UHMWPE | 33.4 | 0.09 | 1,205,000 | ~0 |

Similar results were obtained at $1.25\times10^6$ cycles.

Decalin™ provides additional wear resistance. Clearly, the pre-wear damage mechanisms have been altered, and it is believed that wear may be further postponed and, possibly, reduced in rate once it begins by use of the present methods.

From the appearance of the DLC-UHMWPE contact surface, it appears that localized adhesion takes place as the DLC rider passes over the polyethylene surface, possibly pulling out the soft (lower molecular weight) constituent on a gradual cyclic basis. However, the adhesive contact force is insufficient to fail the pulled out microstructure, at least before $1.25 \times 10^6$ cycles. The prewear structures shown above do not resemble the individual "mountain peak" topography associated with submicrometer particle production; therefore, it is possible that a different particle generation mechanism, hence a different particle size distribution, will prevail. Since osteolytic destruction of the bone-biomaterial interface is induced principally by submicrometer particles, the production of larger average size particles may result in reduced osteolytic destruction. The possibility for improvement seems greatest for DLC against solvent-immersed UHMWPE. Here, soft-phase fibrillation was eliminated, there is a high likelihood that wear can be postponed further, that the eventual wear mechanism and rate will be altered, and that the wear particle size distribution will correspond to larger particles, i.e., on the order of the hard semicrystalline domains. Moreover, since Decalin™ penetrates a significant fraction of a millimeter into the UHMWPE, these effects should persist throughout the wear process.

One of skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process for treating an ultra-high molecular weight polyethylene component to reduce frictional shearing off of fibrils from said component comprising:

immersing said ultra-high molecular weight polyethylene component in an organic solvent for a first amount of time and at a temperature sufficient to dissolve polyethylene fibrils that are susceptible to frictional shearing off during use but insufficient to result in damage due to swelling of said ultra-high molecular weight polyethylene component, said organic solvent being selected from the group consisting of an aromatic hydrocarbon, an alicyclic hydrocarbon, an aliphatic hydrocarbon, and a mixture thereof; and exposing said component to a vacuum of $10^{-1}$–$10^{-5}$ torr for a second amount of time sufficient to remove residual solvent.

2. The process of claim 1 wherein said first amount of time comprises at least 30 seconds.

3. The process of claim 1 wherein said second amount of time comprises at least 8 hours.

4. The method of claim 1 wherein said temperature is between about 30°–100° C.

5. The method of claim 1 wherein said temperature is between about 30°–50° C.

6. The method of claim 2 wherein said temperature is between about 30°–100° C.

7. The method of claim 2 wherein said temperature is between about 30°–50° C.

8. The method of claim 3 wherein said temperature is between about 30°–100° C.

9. The method of claim 3 wherein said temperature is between about 30°–50° C.

10. A method for making an orthopaedic implant comprising a metal alloy substrate in frictional contact with an ultra-high molecular weight polyethylene component, said method comprising the steps of:

immersing said ultra-high molecular weight polyethylene component in an organic solvent for a first amount of time and at a temperature sufficient to dissolve polyethylene fibrils that are susceptible to frictional shearing off during use but insufficient to result in damage due to swelling of said ultra-high molecular weight polyethylene component, said organic solvent being selected from the group consisting of an aromatic hydrocarbon, an alicyclic hydrocarbon, an aliphatic hydrocarbon, and a mixture thereof;

exposing said component to a vacuum at a pressure of about $10^{-3}$ torr for a second amount of time sufficient to remove residual solvent;

exposing a substrate comprising a metal alloy selected from the group consisting of cobalt, nickel, titanium, zirconium, chromium, molybdenum, tungsten, platinum, palladium, and combinations thereof, to a vacuum at a pressure of about $10^{-5}$ torr or less;

heating said substrate to about 300° C. or, if said metal alloy is temperature sensitive, to a highest temperature acceptable for said metal alloy;

depositing silicon onto said substrate to a thickness of between about 100–200 nm;

substantially simultaneously bombarding said deposited silicon with a first energetic beam of nitrogen ions having a first energy of between about 10–30 keV at a first ion density and for a third amount of a time sufficient to form an inner bonding layer of metal-silicide cohesively bonded to an outer layer of silicon;

cooling said substrate to about 80° C.;

condensing a diamond-like carbon precursor onto said outer layer of silicon for a fourth amount of time sufficient to form a film of precursor molecules on said outer layer of silicon;

substantially simultaneously bombarding said diamond-like carbon precursor with a second energetic beam of nitrogen ions having a second energy of between about 10–30 keV at a second ion density and for a fifth amount of time sufficient to form a silicon carbide bonding layer cohesively bonded to an outer coating of diamond-like carbon.

11. A method for coating a metal alloy substrate with diamond-like carbon comprising:

exposing said metal alloy substrate to a vacuum at a pressure of about $10^{-5}$ torr or less;

heating said substrate to a first temperature of about 300° C. or, if said metal alloy is temperature sensitive, to a highest temperature acceptable for said metal alloy;

depositing silicon onto said substrate in an amount sufficient to form an inner bonding layer of metal-silicide cohesively bonded to an outer layer of silicon;

substantially simultaneously bombarding said deposited silicon with a first energetic beam of ions at a first energy, a first ion density, and for a first amount of time sufficient to form said inner metal-silicide bonding layer cohesively bonded to said outer layer of silicon;

condensing a diamond-like carbon precursor onto said outer layer of silicon at a second temperature and for a second amount of time sufficient to form a film of precursor molecules on said outer layer of silicon, wherein said second temperature is sufficiently low that said diamond-like carbon precursor is not vaporized off of said substrate;

substantially simultaneously bombarding said diamond-like carbon precursor with a second energetic beam of ions at a second energy, a second ion density, and for a third amount of time sufficient to form an inner silicon carbide layer cohesively bonded to an outer coating of diamond-like carbon.

12. The method of claim 11 wherein said first and second beam of ions comprise ions selected from the group consisting of nitrogen, argon, hydrogen, silicon, methane, helium, neon, and combinations thereof.

13. The method of claim 11 wherein said second beam of ions comprises nitrogen ions.

14. The method of claim 11 wherein said first energy and said second energy are between about 10–30 keV.

15. The method of claim 11 wherein said second temperature is about 80° C.

16. The method of claim 13 wherein said second temperature is about 80° C.

17. The method of claim 11 wherein said silicon is deposited onto said substrate to a thickness of between about 100–200 nm.

18. The method of claim 12 wherein said silicon is deposited onto said substrate to a thickness of between about 100–200 nm.

19. A method for coating a metal alloy substrate with diamond-like carbon comprising:

providing a substrate comprised of a metal alloy selected from the group consisting of cobalt, nickel, titanium, zirconium, chromium, molybdenum, tungsten, platinum, palladium, and combinations thereof;

exposing said substrate to a vacuum at a pressure of about $10^{-5}$ torr or less;

heating said substrate to a first temperature of about 300° C. or, if said metal alloy is temperature sensitive, to a highest temperature acceptable for said metal alloy;

depositing silicon onto said substrate in an amount sufficient to form an inner bonding layer of metal-silicide cohesively bonded to an outer layer of silicon;

substantially simultaneously bombarding said deposited silicon with a first energetic beam of ions at a first energy, a first ion density, and for a first amount of time sufficient to form said inner metal-silicide bonding layer cohesively bonded to said outer layer of silicon;

condensing a diamond-like carbon precursor onto said outer layer of silicon at a second temperature and for a second amount of time sufficient to form a film of precursor molecules on said outer layer of silicon, wherein said second temperature is sufficiently low that said diamond-like carbon precursor is not vaporized off of said substrate;

substantially simultaneously bombarding said diamond-like carbon precursor with a second energetic beam of ions at a second energy, a second ion density, and for a third amount of time sufficient to form an inner silicon carbide layer cohesively bonded to an outer coating of diamond-like carbon.

20. The method of claim 19 wherein said second beam of ions comprises nitrogen ions.

21. The method of claim 19 wherein said first energy and said second energy are between about 10–30 keV.

22. The method of claim 19 wherein said second temperature is about 80° C.

23. The method of claim 19 wherein said silicon is deposited onto said substrate to a thickness of between about 100–200 nm.

24. A method for making an orthopaedic implant comprising a metal alloy substrate in frictional contact with an ultra-high molecular weight polyethylene component, said method comprising the steps of:

exposing a substrate comprising a metal alloy selected from the group consisting of cobalt, nickel, titanium, zirconium, chromium, molybdenum, tungsten, platinum, palladium, and combinations thereof, to a vacuum at a pressure of about $10^{-5}$ torr or less;

heating said substrate to about 300° C. or, if said metal alloy is temperature sensitive, to a highest temperature acceptable for said metal alloy;

depositing silicon onto said substrate to a thickness of between about 100–200 nm;

substantially simultaneously bombarding said deposited silicon with a first energetic beam of nitrogen ions having a first energy of between about 10–30 keV at a first ion density and for a third amount of a time sufficient to form an inner bonding layer of metal-silicide cohesively bonded to an outer layer of silicon;

cooling said substrate to about 80° C.;

condensing a diamond-like carbon precursor onto said outer layer of silicon for a fourth amount of time sufficient to form a film of precursor molecules on said outer layer of silicon;

substantially simultaneously bombarding said diamond-like carbon precursor with a second energetic beam of nitrogen ions having a second energy of between about 10–30 keV at a second ion density and for a fifth amount of time sufficient to form a silicon carbide bonding layer cohesively bonded to an outer coating of diamond-like carbon.

25. A method for coating a metal alloy orthopaedic component with diamond-like carbon comprising:

exposing said metal alloy orthopaedic component to a vacuum at a pressure of about $10^{-5}$ torr or less;

heating said component to a first temperature of about 300° C. or, if said metal alloy is temperature sensitive, to a highest temperature acceptable for said metal alloy;

depositing silicon onto said component in an amount sufficient to form an inner bonding layer of metal-silicide cohesively bonded to an outer layer of silicon;

substantially simultaneously bombarding said deposited silicon with a first energetic beam of ions at a first energy, a first ion density, and for a first amount of time sufficient to form said inner metal-silicide bonding layer cohesively bonded to said outer layer of silicon;

condensing a diamond-like carbon precursor onto said outer layer of silicon at a second temperature and for a second amount of time sufficient to form a film of precursor molecules on said outer layer of silicon, wherein said second temperature is sufficiently low that said diamond-like carbon precursor is not vaporized off of said component;

substantially simultaneously bombarding said diamond-like carbon precursor with a second energetic beam of ions at a second energy, a second ion density, and for a third amount of time sufficient to form an inner silicon carbide layer cohesively bonded to an outer coating of diamond-like carbon.

26. The method of claim 25 wherein said second beam of ions comprises nitrogen ions.

27. The method of claim 25 whereto said first energy and said second energy are between about 10–30 keV.

28. The method of claim 26 wherein said first energy and said second energy are between about 10–30 keV.

29. The method of claim 25 wherein said silicon is deposited onto said substrate to a thickness of between about 100–200 nm.

30. A method for coating a metal alloy orthopaedic component with diamond-like carbon comprising:

provided an orthopaedic component comprised of a metal alloy selected from the group consisting of cobalt, nickel, titanium, zirconium, chromium, molybdenum, tungsten, platinum, palladium, and combinations thereof;

exposing said component to a vacuum at a pressure of about $10^{-5}$ torr or less;

heating said component to a first temperature of about 300° C. or, if said metal alloy is temperature sensitive, to a highest temperature acceptable for said metal alloy;

depositing silicon onto said component in an amount sufficient to form an inner bonding layer of metal-silicide cohesively bonded to an outer layer of silicon;

substantially simultaneously bombarding said deposited silicon with a first energetic beam of ions at a first energy, a first ion density, and for a first amount of time sufficient to form said inner metal-silicide bonding layer cohesively bonded to said outer layer of silicon;

condensing a diamond-like carbon precursor onto said outer layer of silicon at a second temperature and for a second amount of time sufficient to form a film of precursor molecules on said outer layer of silicon, wherein said second temperature is sufficiently low that said diamond-like carbon precursor is not vaporized off of said component;

substantially simultaneously bombarding said diamond-like carbon precursor with a second energetic beam of ions at a second energy, a second ion density, and for a third amount of time sufficient to form an inner silicon carbide layer cohesively bonded to an outer coating of diamond-like carbon.

31. The method of claim 30 wherein said second beam of ions comprises nitrogen ions.

32. The method of claim 30 wherein said first energy and said second energy are between about 10–30 keV.

33. The method of claim 31 wherein said first energy and said second energy are between about 10–30 keV.

34. The method of claim 30 wherein said silicon is deposited onto said substrate to a thickness of between about 100–200 nm.

35. A process for treating an ultra-high molecular weight polyethylene orthopaedic component to reduce frictional shearing off of fibrils from said component comprising:

immersing said ultra-high molecular weight polyethylene orthopaedic component in an organic solvent for a first amount of time and at a temperature sufficient to dissolve polyethylene fibrils that are susceptible to frictional shearing off during use but insufficient to result in damage due to swelling of said ultra-high molecular weight polyethylene orthopaedic component, said organic solvent being selected from the group consisting of an aromatic hydrocarbon, an alicyclic hydrocarbon, an aliphatic hydrocarbon, and a mixture thereof; and exposing said component to a vacuum of $10^{-1}$–$10^{-5}$ torr for a second amount of time sufficient to remove residual solvent.

36. The process of claim 35 wherein said first amount of time comprises at least seconds.

37. The process of claim 35 wherein said second amount of time comprises at least 8 hours.

38. The process of claim 36 wherein said second amount of time comprises at least 8 hours.

\* \* \* \* \*